United States Patent [19]

Cargill

[11] 4,095,971
[45] Jun. 20, 1978

[54] TOBACCO SUCKER CONTROL

[75] Inventor: Roland L. Cargill, Kendall Park, N.J.

[73] Assignee: Rhodia, Inc., New York, N.Y.

[21] Appl. No.: 775,466

[22] Filed: Mar. 8, 1977

[51] Int. Cl.² .............................................. A01N 9/20
[52] U.S. Cl. ....................................................... 71/78
[58] Field of Search .................................. 71/78, 111

[56] References Cited

U.S. PATENT DOCUMENTS

| 3,253,904 | 5/1966 | Harrison | 71/111 |
|---|---|---|---|
| 3,890,130 | 6/1975 | George et al. | 71/111 X |

FOREIGN PATENT DOCUMENTS

| 1,249,434 | 8/1960 | France | 71/111 |
|---|---|---|---|
| 78,254 | 6/1962 | France | 71/111 |

*Primary Examiner*—Catherine L. Mills
*Attorney, Agent, or Firm*—Robert E. Burns; Emmanuel J. Lobato; Bruce L. Adams

[57] ABSTRACT

A process is described for the inhibition of axillary buds in tobacco plants which comprises the steps of applying an axillary bud-inhibiting amount of carbetamide in an agriculturally acceptable composition, to tobacco plants and their environs.

10 Claims, No Drawings

TOBACCO SUCKER CONTROL

FIELD OF THE INVENTION

This invention relates to the chemical control and inhibition of buds or suckers in tobacco culture and more particularly to the chemical inhibition of primary and secondary axillary buds by the systemic application of carbetamide to tobacco plants.

BACKGROUND OF THE INVENTION

Over the years, tobacco growers have utilized various agricultural practices to improve the quality and yield of their crop. Removal of the tobacoo tops has been historically practiced as one method of increasing the yield of tobacco leaves. Upon removal of the plant tops, the energy and growth normally translocated to the plant tops for inflorescence is diverted into the leaves, resulting in greater numbers and size of the leaves, thus increasing the economic yield. The nature of any plant is to reproduce itself; therefore, when the tobacco infloresence is removed, a physiological process known as 'apical dominance' is triggered. This phenomena results in accelerated growth of the uppermost axillary buds (suckers) which exists at each leaf axil. If allowed to develop unhindered, these suckers would each develop infloresence and in turn result in leaf yield reductions. In earlier years this sucker growth was removed by hand.

In recent years, tobacco growers in the U.S.A. have relied on chemicals to control and minimize sucker growth.

The major portion of flue-cured and burley tobacco (~820,000 acres) is chemically treated annually for the control of suckers.

One chemical method of sucker (axillary bud) control consists in the topical contact application of fatty alcohols (nominal $C_8$-$C_{10}$), mineral oils and similar inhibiting agents directly to the axillary buds before and during their initial development stages. These topical agents have some phytotoxic action on the leaves and thus should be carefully applied preferably to the buds. Leaf contact should be avoided. Generally these agents are applied to the initial "topping" areas and by dripping down the stem these agents contact the axillary buds adjacent to the main stem. However, any contact with the leaves by the dripping agents may cause chlorosis and other phytotoxic effects as well as other degradation of leaf quality. Further, as these contact agents drip and accumulate at the base, they often have caused necrosis of the entire stem base and kill the plant. A further drawback to the present topical chemical budinhibition method is that some of these aspects require the skillful manual application of the agent at the required location and require considerable fairly skilled hand labor which is economically unsuitable in large scale tobacco culture.

Another method for sucker control in tobacco cultivation has been by the systemic application, after topping, of maleic hydrazide (1,2-Dihydro-3,6-pyridazindione). The maleic hydrazide (MH) is applied, in the form of its salts or amine complexes, by spraying onto the plants after the manual topping of the initial inflorescence. The maleic hydrazide (MH) is systemically absorbed through the leaves and has been effective for inhibiting the development of the axillary buds.

However, as noted in the Merck Index 8th Edition, Page 640, this material, as are most hydrazides, is toxic. It has produced CNS disturbances under acute exposure conditions and liver damage on chronic exposure, in experimental animals. Thus use of this agent under field conditions, should be properly supervised. Use of the material despite its economic importance is under review and in some countries is prohibited.

THE INVENTION

I have discovered that when Carbetamide, and its agriculturally acceptable salts and complexes, as active ingredient, when applied via suitable compositions in controlled amounts of at a rate of from 0.25 to 20 lbs of active ingredient per acre to growing tobacco plants will inhibit the development of inflorescence and axillary buds. This bud-inhibition is evidenced by the absence of or decreased size and number of buds or "suckers" as compared to topped tobacco plants.

The preferred compound for use in this process is Carbetamide having the formula

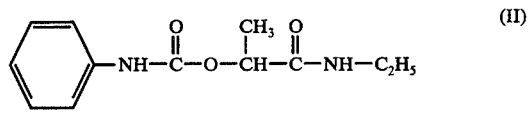

(II)

also known as D-N-ethyl lactamide carbanilate, or N-Phenyl-1-(ethylcarbamoyl)ethylcarbamate(D-isomer).

The name Carbetamide is a "common name" approved by ISO and ANSI.

Carbetamide is a selective herbicide which has been widely used in the cultivation of forage legumes and garden legumes as well as in rapeseed, caraway and fennel cultivation. It is also used for weed control in fallow land, orchards, vineyards, and nurseries.

Carbetamide has a good safety record with an acute $LD_{50}$ in rats of 11,000 mgm/kg. It is practically devoid of chronic toxicity in long term exposure. Further topical application in the rabbit eye (5 mgm) and to rabbit skin (5% cream) indicates absence of irritant effects.

DETAILED DESCRIPTION

Carbetamide, which is the effective sucker inhibitor, functions by being translocated from the areas of absorbtion to the meristematic regions of the tobacco plant where it blocks or inhibits the growth of the axillary buds by modifying the meristematic activity. The carbetamide when applied, in the amounts set forth, of from 0.25 lb ai to 20 lb ai/acre to the leaves and to the soil where it is absorbed by the plant, has specific meristematic growth regulating activity as regards the suckers. The growth of the suckers is either completely prevented or is halted at the rudimentary stages with little phytotoxic effects on the leaves. At higher application levels, in the range above 20 lb/acre the compound acts as a general herbicide and begins to be phytotoxic to the entire plant. Such herbicidal effects are known and have been described in French Pat. No. 1,249,434 which issued in 1959 and its Patent of Addition No. 78,254 which issued on May 21, 1962.

METHODS OF APPLICATION

The agent of this invention has limited solubility. Carbetamide is soluble in water to the extent of about 3.5 gms/litr. It is thus preferred to apply the sucker inhibiting agent of this invention by dispersion in liquid or solid media at concentrations of about 0.5 to 50%. To achieve such concentrations in liquid media the carbetamide is preferably applied in the form of an emulsified dispersion in water via emulsion of a solution in a solvent for the active material. Suitable solvents include acetone; DMF; lower alkanols, such as methanol or denatured ethanol; chlorinated hydrocarbons, such as methylene chloride; aromatic solvents, such as toluene and xylene; and cyclic alcohols such as cyclohexanone.

Emulsiers for the preparation of such dispersions are agriculturally acceptable surfactants which include the commonly used cationic, anionic, non-ionic or zwitter-ion surfactants as for example, the salts of the polyacrylic acid, ligno-sulfonic acids, condensates of ethylene oxide in fatty alcohols, acids and amines.

The solvents, actives and surfactants are prepared into emulsifiable concentrates which are then diluted with water, before application, to proper concentration. The liquid concentrate compositions are preferred for the preparation of dispersions for spray application. However, such concentrates may be modified for dispersion application to the tobacco plants via dusts, aerosols, mists, or fogs or via irrigation. Such methods for media preparation for the application of agricultural materials are art-recognized.

The active material of this invention may also be applied to the tobacco plants in solid form i.e. via wettable powders, dusts or granules. These are applied by dusting or dispersing the solids, in requisite amounts, onto the tobacco plants or their adjacent environs i.e. the soils, or during watering.

The emulsifiable concentrate wettable powders, dusts, and granules are formulated initially into concentrates comprising 1–95% of active material with the balance consisting of wetting agents, adsorbants, binders, penetration agents, stabilizers, dispersants and other agriculturally acceptable adjuvants used for such modes and media for application of agricultural agents. Other agricultural actives may also be included in the formulation for simultaneous application, including fungicides, fertilizers, other growth stimulants, insecticides, etc. Before use, the concentrates are diluted with agriculturally acceptable diluents useful for such modes of application. They usually include water, clays, sands, silicates, waxes, fertilizers.

The concentrate compositions, liquid, solid or semi-solid are diluted before application to the plants to ensure uniform distribution to the tobacco plants and the areas where they are growing. The degree of dilution is controlled by the mode of application. When carbetamide is sprayed in liquid form via aqueous dispersion, the concentrate level of active ingredient may range from 0.5 to 50 wt% ai (active ingredient). The preferred concentrate range is from 2 to 10 wt % ai. The effective level of application of carbetamide for inhibition control of tobacco plant suckers is an application of from 0.25 to 10 lbs ai per acre at the proper time with levels of 1 to 4 lbs ai preferred. Above about 10 lb ai per acre chlorosis becomes undesirably evident. At lower than 0.25 lb ai/acre the degree of sucker inhibition is too low to be economically acceptable.

As described above, the preferred compound carbetamide, when applied in the stated range in agriculturally acceptable compositions including the common agricultural vehicles and adjuvants is effective for control of tobacco sucker growth. The material may be applied to tobacco plants that are in the initial bud stage of floral development up to the stage of full floral development. It may be applied as a chemical "topical agent" to eliminate the manual "topping" of the initial apical inflorescence or it may be applied after the "topping". When applied as a chemical topping agent, it should be applied before inflorescence has become well developed. When applied with manual topping, it should be applied soon, before or after, in order to inhibit the development of the axilly budding that is initiated as a result of apical dominance phenomena. The preferred stage of tobacco growth for the application axillary bud-inhibiting agent is when the plants are in the 25 to 50% floral development stage of growth. It may be applied before, after or instead of the removal of the plant tops.

The liquid formulations of Carbetamide may be applied by hand methods such as hand spraying, sprinkling cans etc. but in large scale cultivation, mechanical self-propelled agricultural sprayers are used. The liquids may also be distributed by foggers. The solids may be dusted or broadcast by granule dispersers or mixed into fertilizer dressings before watering. Wettable powders or granules are preferred for application of solid agents. The solids are used at about the same concentration of active ingredient with adjustment made for slower absorption.

The process of this invention includes the application of one or more of the above-mentioned systemically-acting compounds alone or in conjunction with the topical-acting compounds such as the aforementioned mineral oils or fatty alcohols ($C_8$–$C_{12}$) materials. These latter provide a direct contact kill of the tobacco suckers. Thus the combination of the systemic and topical sucker control agents may provide more complete and economic control of the sucker problem in tobacco cultivation.

As mentioned above, Carbetamide is less toxic to mammalian species than the previously used common systemic sucker control agents and thus is safer for use by unskilled agricultural workers. Further, in the absence of significant toxicity, residues of the sucker control agents of this invention on the tobacco would provide a significantly lower health and environmental hazard to the processors and ultimate users of tobacco.

The invention will be demonstrated by the following examples. The examples are merely illustrative of the practice of the invention. All mentioned or art-recognized equivalent materials or steps are intended for practice in association with this invention.

| Emulsifiable concentrate | |
|---|---|
| Carbetamide | 200 parts (Wt) |
| Xylene | 180 parts |
| Nonylphenol oxyethyl-17-ethylene oxide | 200 parts |
| Cyclohexanone to | 1000 parts |

The above emulsifiable concentrate or an equivalent thereof, was diluted as indicated for field use in the following examples.

Field Tests

The tests in the following examples were carried out in commercial tobacco plots. The active ingredients (ai) were applied at the indicated rats per acre. For purposes of comparison, control and comparison plots were also observed. In the control plots the tobacco plants were merely topped but no further chemical bud control agents were applied. In the comparison plots Maleic hydrazide (diethanolamine salt) (MH) in the present tentatively approved concentration of 3 lbs ai/acre was applied.

EXAMPLE 1

Tobacco plants (variety Flue-cured) were planted on the 25th of May in sandy soil in Virginia.

The treatments were carried out at the time of flowering on the 18th of August by spraying the tobacco plants with a mixture obtained by diluting with water the emulsifiable concentrate containing the carbetamide to yield the required application rate.

The comparative test was carried out under the same conditions, using an emulsifiable concentrate of the same composition in which the carbetamide was replaced by MH i.e. the diethanoamine salt of maleic hydrazide.

The efficacy on the buds was evaluated on September 20 when any remaining buds were cut off and weighed.

The phytotoxicity was evaluated by visual observation of the rate of chlorosis of the treated leaves, at 24 hours after treatment and at 8 days after treatment. In the case of this example, no chlorosis appeared during the course of the two visual observations, in either the carbetamide or diethanolamine maleic hydrozide salt treatments.

EXAMPLE 2

Flue-cured tobacco plants grown in North Carolina were treated with carbetamide (2.5 lbs/gal EC) and MH (3.0 lbs/gal and EC) for control of tobacco suckers. The plants were topped prior to treatment and suckers longer than one inch were removed. The materials were applied with a $CO_2$ backpack sprayer at about 20 psi at a speed of 2 mph which delivered the equivalent of 25 gallons of spray solution per acre. Results were as follows:

TABLE FOR EXAMPLE 2

| COMPOUND | RATE (lbai/A) | CROP PHYTOTOXICITY [1] | | CROP EFFICACY (31 days post treatment) | | % Sucker Control |
|---|---|---|---|---|---|---|
| | | 1 Day | 7 Days | No. of Suckers per 10 Plants | Green Wt. of Suckers per 10 Plants (GMS) | |
| Carbetamide | 1.0 | 0 | 20 | 5 | 36.0 | 97 |
| | 2.0 | 0 | 40 | 7 | 19.9 | 98 |
| | 4.0 | 0 | 40 | 5 | 14.0 | 99 |
| MH | 3.0 | 0 | 0 | 4 | 26.7 | 98 |
| Topped Not Suckered Control | — | 0 | 0 | 47 | 1260.5 | 0 |

[1]percent chlorosis

The following table shows the bud weights in the case of plants treated with carbetamide, the plants treated with the diethanolamine salt of maleic hydrazide, and the untreated plants:

| | Dose of active ingredient in kg/ha | weight of buds (in gms per 10 plants) |
|---|---|---|
| Treatment with Carbetamide | 1.0 | 290 |
| | 2.0 | 60 |
| | 4.0 | 0 |
| Treatment with diethanolamine salt of maleic hydrazide | 3.0 | 7 |
| Untreated control | 0 | 2724 |

EXAMPLE 3

Flue-cured tobacco plants grown in Virginia were treated with carbetamide (2.5 lbs/gal EC) and MH (3.0 lbs/gal EC) for control of tobacco suckers. The procedure of Example 2 was followed. Results were as follows:

TABLE FOR EXAMPLE 3

| COMPOUND | RATE (lbai/A) | CROP PHYTOTOXICITY [1] | | CROP EFFICACY (33 days post treatment) | | % Sucker Control |
|---|---|---|---|---|---|---|
| | | 1 Day | 9 Days | No. of Suckers per 10 Plants | Green Wt. of Suckers per 10 Plants (GMS) | |
| Carbetamide | 1.0 | 0 | 0 | 4 | 290 | 89 |
| | 2.0 | 0 | 0 | 3 | 60 | 98 |
| | 4.0 | 0 | 0 | 0 | 0 | 100 |
| MH | 3.0 | 0 | 0 | 1 | 7 | 99 |
| Topped Not Suckered Control | — | 0 | 0 | 28 | 2724 | 0 |

[1]percent chlorosis

EXAMPLE 4

Coker flue-cured tobacco plants grown in North Carolina were treated with carbetamide (2.5 lbs/gal EC) and MH (3.0 lbs/gal EC) to control tobacco suckers. The procedure of Example 2 was followed. Results were as follows:

TABLE FOR EXAMPLE 4

| COMPOUND | RATE (lbai/A) | CROP PHYTOTOXICITY [1] | | CROP EFFICACY (45 days post treatment) | | % Sucker Control |
|---|---|---|---|---|---|---|
| | | 2 Days | 45 Days | No. of Suckers per Plant Avg. | Green Wt. of Suckers per Plant (GMS) | |
| Carbetamide | 1.0 | 0 | 0 | 1.2 | 102.0 | 93 |
| | 2.0 | 0 | 0 | 0.9 | 49.5 | 97 |
| | 4.0 | 0 | 0 | 0.9 | 30.6 | 98 |
| MH | 3.0 | 0 | 0 | 1.3 | 126.1 | 91 |
| Topped Not Suckered | | | | | | |

-continued

TABLE FOR EXAMPLE 4

| COMPOUND | RATE (lbai/A) | CROP PHYTOTOXICITY [1] | | CROP EFFICACY (45 days post treatment) | | % Sucker Control |
|---|---|---|---|---|---|---|
| | | 2 Days | 45 Days | No. of Suckers per Plant Avg. | Green Wt. of Suckers per Plant (GMS) | |
| Control | — | 0 | 0 | 6.0 | 1422.0 | 0 |

[1] 0 = no injury; 5 - severe injury.

EXAMPLE 5

McNair flue-cured tobacco plants, grown in Georgia, were treated with carbetamide (2.5 lbs/gal EC) and MH (3.0 lbs/gal EC) for control of tobacco suckers. Procedure of Example 2 was followed. Results were as follows:

TABLE FOR EXAMPLE 5

| COMPOUND | RATE (lbai/A) | CROP PHYTOTOXICITY | | | | Green Wt. of Suckers 10 Plants (GMS) | CROP EFFICACY Percent Sucker Control | | |
|---|---|---|---|---|---|---|---|---|---|
| | | 1 Day | 7 Days | 14 Days | 30 Days | | 7 Days[2/] | 14 Days[2/] | 30 Days |
| Carbetamide | 1.0 | 0 | 0 | 0 | 0 | 885 | 0 | 60 | 80 |
| | 2.0 | 0 | 0 | 0 | 1 | 548 | 90 | 95 | 87 |
| | 4.0 | 0 | 1 | 1 | 1 | 399 | 95 | 95 | 91 |
| | 8.0 | 0 | 2 | 2 | 2 | 0 | 98 | 100 | 100 |
| MH | 3.0 | 0 | 0 | 0 | 1 | 42 | 95 | 98 | 99 |
| Topped Not Suckered Control | — | 0 | 0 | 0 | 0 | 4358 | 0 | 0 | 0 |

[1/] crop injury scale - 0 = no injury; 5 = complete necrosis
[2/] % sucker control based on visual observations.

EXAMPLE 6

Burley tobacco plants, grown in West Virginia, were treated with carbetamide (2.5 lbs/gal EC) and MH (3.0 lbs/gal EC) to control tobacco suckers. Procedure of Example 2 was followed. Results were as follows:

TABLE FOR EXAMPLE 6

| COMPOUND | RATE (lbai/A) | CROP PHYTOTOXICITY [1] | | | | Green Wt. of Suckers 10 Plants (GMS) | CROP EFFICACY | | # of Suckers 10 Plants |
|---|---|---|---|---|---|---|---|---|---|
| | | 1 Day | 7 Days | 14 Days | 28 Days | | % Sucker Control | | |
| | | | | | | | 14 Days[2] | 28 Days | |
| Carbetamide | 1.0 | 0 | 0 | 0 | 0 | 793.8 gm. | 90 | 86 | 29 |
| | 2.0 | 0 | 0 | 0 | 0 | 283.5 | 98 | 95 | 18 |
| | 4.0 | 0 | 0 | 0 | 0 | 226.8 | 98 | 96 | 19 |
| MH | 3.0 | 0 | 0 | 0 | 0 | 793.8 | 95 | 86 | 100 |
| Topped Not Suckered Control | — | 0 | 0 | 0 | 0 | 5760.0 | 0 | 0 | 96 |

[1] 0 = no injury; 5 = severe injury
[2] evaluation based on visual observation.

EXAMPLE 7

Burley tobacco plants, grown in Kentucky, were treated with carbetamide (2.5 lbs/gal EC) and MH (3.0 lbs/gal EC) to control tobacco suckers. Procedure of Example 2 was followed. Results were as follows:

TABLE FOR EXAMPLE 7

| COMPOUND | RATE (lbai/A) | CROP PHYTOTOXICITY [1] | | | | Green Wt. of Suckers per Plant (GMS) | CROP EFFICACY | | # of Sucker/ Plant |
|---|---|---|---|---|---|---|---|---|---|
| | | 1 Day | 7 Days | 14 Days | 28 Days | | % Sucker Control | | |
| | | | | | | | 14 Days[2] | 28 Days | |
| Carbetamide | 1.0 | 0 | 0 | 0 | 0 | 272 | 85 | 65 | 9.1 |
| | 2.0 | 0 | 0 | 0 | 0 | 170 | 95 | 78 | 5.3 |
| | 4.0 | 0 | 0 | 0 | 0 | 68 | 98 | 91 | 3.1 |
| MH | 3.0 | 0 | 0 | 0 | 0 | 465 | 90 | 41 | 7.8 |
| Topped Not Suckered Control | — | 0 | 0 | 0 | 0 | 782 | 0 | 0 | 5.5 |

[1] 0 = no injury; 5 = severe injury
[2] evaluation based on visual observation

What is claimed:

1. A process for the inhibition of axillary budding in tobacco plants which comprises the steps of topping the plant during the development stage of apical influorescence and applying to said plant or its environs, at about the time of said topping, an axillary budding-inhibiting amount of an agriculturally acceptable composition containing as active budding-inhibiting agent the D isomer of 2-phenylcarlamoyloxy-N-ethylpropionamide.

2. The process according to claim 1 wherein said composition is applied before said topping step.

3. The process according to claim 1 where said composition is applied in conjunction with said topping step.

4. The process according to claim 1 wherein said composition is applied after said topping step.

5. The process according to claim 1 wherein said composition is applied to stands of tobacco in amounts equivalent to 0.25 to 10 lb of carbetamide per acre.

6. The process according to claim 5 wherein said application is by spraying of said agriculturally acceptable composition is liquid form unto said plants and their environs.

7. The process according to claim 5 wherein said agriculturally acceptable composition in the form of wettable powder or granules is applied by spreading to the plants and the adjacent soil for systemic absorbtion.

8. The process according to claim 5 wherein said carbetamide containing composition is applied in amounts of from 1 to 4 lbs per acre.

9. A process for the inhibition of inflorescence in tobacco plants which comprises the steps of applying an inflorescence-inhibiting amount of carbetamide in an agriculturally acceptable composition, to tobacco plants and their environs.

10. A process according to claim 1, in which said composition is applied within the period of the initial bud stage of floral development of said tobacco plant to the stage of full floral development.

* * * * *